(12) United States Patent
Silberstein

(10) Patent No.: US 6,792,304 B1
(45) Date of Patent: Sep. 14, 2004

(54) MASS COMMUNICATION ASSESSMENT SYSTEM

(75) Inventor: Richard B. Silberstein, Blackburn (AU)

(73) Assignee: Swinburne Limited (AU)

( * ) Notice: Subject to any disclaimer, the term of this patent is extended or adjusted under 35 U.S.C. 154(b) by 0 days.

(21) Appl. No.: 09/700,295

(22) PCT Filed: May 14, 1999

(86) PCT No.: PCT/AU99/00366

§ 371 (c)(1),
(2), (4) Date: Mar. 15, 2001

(87) PCT Pub. No.: WO99/59470

PCT Pub. Date: Nov. 25, 1999

(30) Foreign Application Priority Data

May 15, 1998 (AU) .................................... PP3548

(51) Int. Cl.[7] .............................. A61B 5/04; A61B 5/06
(52) U.S. Cl. ...................................... 600/544; 600/300
(58) Field of Search .................................. 600/544, 559, 600/300, 303, 558; 200/90; 128/898, 924, 920, 923

(56) References Cited

U.S. PATENT DOCUMENTS

| | | | |
|---|---|---|---|
| 2,860,627 A | 11/1958 | Harden | 128/731 |
| 3,087,487 A | 4/1963 | Clynes | 128/731 |
| 3,498,287 A | 3/1970 | Ertl | 128/731 |
| 3,513,834 A | 5/1970 | Suzuki et al. | 128/731 |
| 3,689,135 A | 9/1972 | Young et al. | 351/39 |
| 3,809,069 A | 5/1974 | Bennett | 128/731 |
| 3,855,998 A | 12/1974 | Hidalgo-Briceno | 128/745 X |
| 3,880,144 A | 4/1975 | Coursin et al. | 128/2.1 |
| 3,892,227 A | 7/1975 | Coursin et al. | 128/2.1 |
| 3,901,215 A | 8/1975 | John | 128/745 X |
| 3,998,213 A | 12/1976 | Price | 128/644 |
| 4,083,365 A | 4/1978 | Yancey | 128/731 |
| 4,094,307 A | 6/1978 | Young, Jr. | 128/731 |
| 4,140,997 A | 2/1979 | Brady | 128/732 |
| 4,201,224 A | 5/1980 | John | 128/731 |
| 4,216,781 A | 8/1980 | John | 128/731 |
| 4,244,376 A | 1/1981 | Fisher et al. | 128/731 |
| 4,304,242 A | 12/1981 | Siarkiewicz et al. | 128/745 |
| 4,407,299 A | 10/1983 | Culver | 128/731 |
| 4,421,122 A | 12/1983 | Duffy | 128/731 |

(List continued on next page.)

FOREIGN PATENT DOCUMENTS

| | | |
|---|---|---|
| FR | 2604889 | 4/1988 |
| WO | WO 87/00745 | 2/1987 |

OTHER PUBLICATIONS

A. Papanicolauo et al., "Prove Evoked Potentials: Theory, Method and Applications," Intern. J. Neuroscience, vol. 24, pp. 107–131 (1984).

Proceedings of the Eleventh Annual Northeast Bioengineering Conference, Mar. 14, 15, 1985, Worcester Polytechnic Institute, Worcester, Massachusetts, Walter S. Kuklinski and William J. Ohley, pp. 128–134.

(List continued on next page.)

Primary Examiner—Daniel Robinson
(74) Attorney, Agent, or Firm—Wolf, Greenfield & Sacks, P.C.

(57) ABSTRACT

A mass communication assessment system (2) communicating a cognitive task to selected remote test sites (12) via a network (10) for providing a two-way communication between the central control site and the remote sites, detecting brain response signals from the subject (40) to the task, and having processing means (16) for computing variations in the brain activity for the subjects at each of the selected sites.

15 Claims, 12 Drawing Sheets

U.S. PATENT DOCUMENTS

| | | | |
|---|---|---|---|
| 4,462,411 A | 7/1984 | Rickards | 128/731 |
| 4,493,327 A | 1/1985 | Bergelson et al. | 128/731 |
| 4,493,539 A | 1/1985 | Cannon, Jr. | 128/731 |
| 4,537,198 A | 8/1985 | Corbett | 128/639 |
| 4,566,464 A | 1/1986 | Piccone et al. | 128/731 |
| 4,570,640 A | 2/1986 | Barsa | 128/741 |
| 4,610,259 A | 9/1986 | Cohen et al. | 128/731 |
| 4,632,122 A | 12/1986 | Johansson et al. | 128/644 |
| 4,632,126 A | 12/1986 | Aguilar | 128/732 |
| 4,649,482 A | 3/1987 | Raviv et al. | 128/731 |
| 4,665,499 A | 5/1987 | Zacharski et al. | 128/731 |
| 4,676,611 A | 6/1987 | Nelson et al. | 128/731 |
| 4,744,029 A | 5/1988 | Raviv et al. | 128/731 X |
| 4,794,533 A | 12/1988 | Cohen | 128/731 X |
| 4,832,480 A | 5/1989 | Kornacker et al. | 128/731 |
| 4,861,154 A | 8/1989 | Sherwin et al. | 128/731 |
| 4,862,359 A | 8/1989 | Trivedi et al. | 364/413.05 |
| 4,869,264 A | 9/1989 | Silberstein | 128/731 |
| 4,878,498 A | 11/1989 | Abrams et al. | 128/731 |
| 4,892,106 A | 1/1990 | Gleeson, III | 128/745 |
| 4,913,160 A | 4/1990 | John | 128/731 |
| 4,932,416 A | 6/1990 | Rosenfeld | 128/731 |
| 4,955,388 A | 9/1990 | Silberstein | 128/731 |
| 4,974,602 A | 12/1990 | Abraham-Fuchs et al. | 128/731 |
| 4,977,896 A | 12/1990 | Robinson et al. | 128/653 R |
| 5,137,027 A * | 8/1992 | Rosenfeld | 600/544 |
| 5,243,517 A * | 9/1993 | Schmidt et al. | 600/544 |
| 5,331,969 A | 7/1994 | Silberstein | 128/731 |
| 5,357,427 A | 10/1994 | Langen et al. | 361/413 |
| 5,406,956 A * | 4/1995 | Farwell | 600/544 |
| 5,730,146 A | 3/1998 | Itil et al. | 128/732 |
| 5,957,859 A * | 9/1999 | Rosenfeld | 600/544 |
| 6,063,028 A * | 5/2000 | Luciano | 600/300 |
| 6,298,263 B1 * | 10/2001 | Sedgwick et al. | 600/544 |

OTHER PUBLICATIONS

Descriptive Linear Modeling of Steady–State Visual Evoked Response by William H. Levinson, Andrew M. Junker and Kevin Kenner, Proceedings of the Twenty–First Annual Conference on Manual Control, Jun. 17–19, 1985, Ohio State University, Columbus Ohio, pp. 1.1–1.16.

J. Ciociari et al., "The Multichannel Electrode Helmet," Proceedings Conference on Engineering And Physical Sciences In Medicine, Melbourne, p. 52 (1987) (Abstract only).

J. Dubinsky et al., "A Simple Dot–Density Topogram Fro EEG," Electroenceph. Clin. Neurophysiol., vol. 48, pp. 473–477 (1980).

R. Galambos et al., "Dynamic Changes in Steady–State Responses," In E. Basar (Ed) Springer Series in Brain Dynamics, I. Springer–Verlag, Berlin Heidelberg, pp. 103–122 (1988).

J. Johnstone et al., "Regional Brain Activity in Dyslexic And Control Children During Reading Tasks: Visual Probe Event–Related Potentials," Brain and Language, vol. 21, p. 233–254 (1984).

A. Junker et al., "The Effect of Task Difficulty On The Steady State Visual Evoked Response," 1986 IEEE, pp. 905–908.

W. R. Klemm et al., "Hemispheric Lateralization And Handedness Correlation Of Human Evoked 'Steady–State' Responses To Patterned Visual Stimuli," Physiological Psychology, vol. 8, pp. 409–416 (1980).

D. Regan, "Steady–State Evoked Potentials, Journal of the Optical Society of America," vol. 67, pp. 1475–1489 (1977).

M. A. Schier et al., "Requirements of a High Spatial Resolution Brain Electrical Activity Data Acquisition System," Neuroscience Letters, Suppl. 30, p. S151 (1988) (Abstract only).

R. B. Silberstein et al., "Topographic Distribution of the Steady State Visually Evoked Potential," Neuroscience Letters, Suppl. 30, p. S123 (1988) (Abstract only).

P. S. Sebel et al., "Evoked Responses—A Neurophysiological Indicator of Depth of Anasthesia?", British Journal of Anaesthesia, vol. 57, No. 9, pp. 841–842 (Sep. 1985).

G. F. Wilson et al., "Steady State Evoked Responses: Correlations With Human Cognition," Psychophysiology, vol. 23, p. 57 (1986) (Abstract only).

"Visual Evoked Response Phase Spectrum as Measure of Latency," J.H. Strickland, Jr., et al., 1985 IEEE, pp. 128–134.

"Monitoring the Level of Anesthesia by Automatic Analysis of Spontaneous EEG Activity," McEwen et al., IEEE Transactions on Biomedical Engineering, Jul. 1975, pp. 299–305.

\* cited by examiner

MASS COMMUNICATION ASSESSMENT SYSTEM

This invention relates to a mass communication assessment system.

The present invention relates to a mass communication assessment system which can be used to provide test material from a central control site to a plurality of test sites. Participants at the test sites can view audiovisual test material or other cognitive tasks and means is provided for assessing the psychological response to the test material. A network such as the Internet can be used to transmit data from the test sites to the central site for processing. Where the Internet is used, it is thought to be feasible to provide hardware and software to a relatively large number of subjects spread over various geographical locations, age groups and other socioeconomic groups. In this way a relatively large number of responses can be obtained from selected demographic groups.

The testing procedures can be used to assess interest in audiovisual material, audio material or the like. Assessments of this type are thought to be of considerable use in the advertising industry, film making and other commercial activities which produce audiovisual, audio or visual material. In this specification this material is referred to by the general term "cognitive task".

According to the present invention there is provided a mass communuication assessment system;

a central control site;

a plurality of remote test sites;

input means at the central control site for inputting signals representative of a cognitive task;

means for communicating the input signals to selected remote test sites via a network for providing two-way communication between the central control site and the remote sites;

receiving means at the remote test sites for receiving the input signals and presenting the cognitive task to a subject;

detecting means at the remote test sites for detecting brain response signals from subject to said cognitive task;

means for communicating said brain response signals to said central control site via the network; and processing means for computing variations in brain activity for the subject at each of said selected sites.

The invention also provides a method of mass assessment of psychological response in a cognitive task for a customer including the steps of:

obtaining input data representing a cognitive task from a customer;

transmitting input data signals representing the cognitive task from a central control site to a plurality of selected test sites remote from the test site over a network;

presenting the cognitive task at each or at least some of the selected test sites;

detecting brain response signals from subjects at the selected test sites;

transmitting brain response signals to the central control site over said network;

computing variations in brain activity of said subjects; and computing output data for the customer representing said variations in brain activity to different parts of said cognitive task.

The invention also provides a data processing system for processing data received from remote test sites, said system including:

input means at a central control site for inputting signals representative of a cognitive task;

means for communicating the input signals to selected remote test sites via a network for transmission of said input signals to selected remote sites for presentation of the cognitive task to subjects at the selected test sites;

means for receiving brain response signals of said subjects transmitted to said central control site via the network; and processing means for computing variations in brain activity for said subjects.

The invention also provides a method of mass assessment of psychological response in a cognitive task for a customer including the steps of:

obtaining data representing a cognitive task from a customer;

transmitting data signals representing the data from a central control site to a plurality of selected test sites remote from the test site over a network;

receiving from the network brain response signals from subjects at the selected test sites to which the cognitive task has been presented;

computing variations in brain activity of said subjects; and generating data for the customer representing said variations in brain activity to different parts of said cognitive task.

The invention also provides a test site for communication with a central control site via a network said site including:

receiving means for receiving input signals via the network from the central control site, said signals being representative of a cognitive task;

presenting means for presenting the cognitive task to a subject;

detecting means for detecting brain response signals from the subject to said cognitive task; and means for communicating said brain response signals to said central control site via the network.

The invention also provides a method of transmitting signals from a remote site to a central control site including the steps of:

receiving data signals representing a cognitive task from the central control site over a network;

presenting the cognitive task to a subject;

detecting brain response signals from the subject; and transmitting brain response signals to the central control site over said network.

In the preferred form of the invention, the network comprises the Internet. In this case it is relatively easy to establish communication between the central control site and a multiplicity of participating remote sites. The remote sites can be equipped with hardware which would enable programs and data to be transmitted to the remote sites for participation in the system.

SUMMARY OF THE INVENTION

It is envisaged that the system can be used to generate commercially valuable information to customers regarding responses to audiovisual material such as television commercials, still conmmercials, film or television presentations, radio advertisements or other audiovisual, visual or audio signals.

It is known to provide an apparatus and method for assessing electrical activity of the brain of a subject by calculation of the steady state visually evoked potential (SSVEP) amplitude and phase for a subject and then to generate signals which represent the response of the brain to a cognitive task. This process can be repeated a number of times for a number of of different subjects as to produce an average or mean response. Reference is made to U.S. Pat. Nos. 4,955,388 and 5,331,969, the content of which is hereby incorporated herein by reference. It has now been realised that by provision of appropriate hardware and software, and by utilisation of the Internet, a very broad spectrum of subjects can readily be accessed. This enables mass assessment of test materials to be conveniently made at a great number of remote sites. The central control site may also include demographic information regarding the sites and their associated subjects thereby providing an opportunity for selection of subjects to a particular input or by ascertaining responses for particular demographic groups of subjects.

BRIEF DESCRIPTION OF THE DRAWINGS

The invention will now be further described with reference to the accompanying drawings, in which.

DETAILED DESCRIPTION

Figure 1:
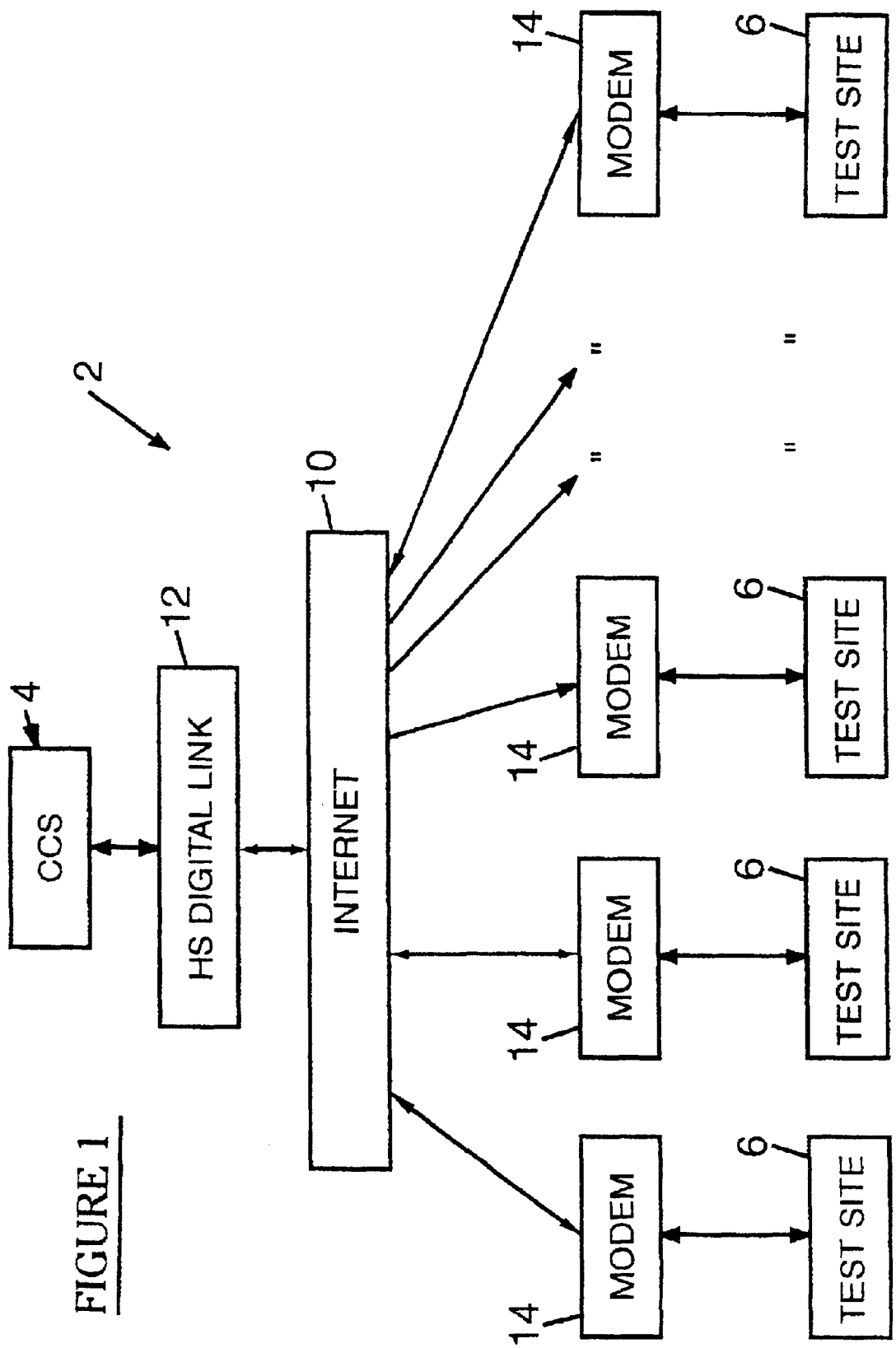
FIG. 1 is a block diagram of a mass communication assessment system of the invention.

FIG. 1 diagrammatically shows a mass communication assessment system 2 of the invention. It comprises a central control site 4 coupled to a plurality of remote test sites 6 by means of a network 8. The network 8 preferably comprises the Internet 10. The central control site 4 is coupled to the Internet by means of a high speed digital link 12 and each of the test sites 6 is connected to the Internet 10 by a modem 14 in the usual way.

Figure 2:
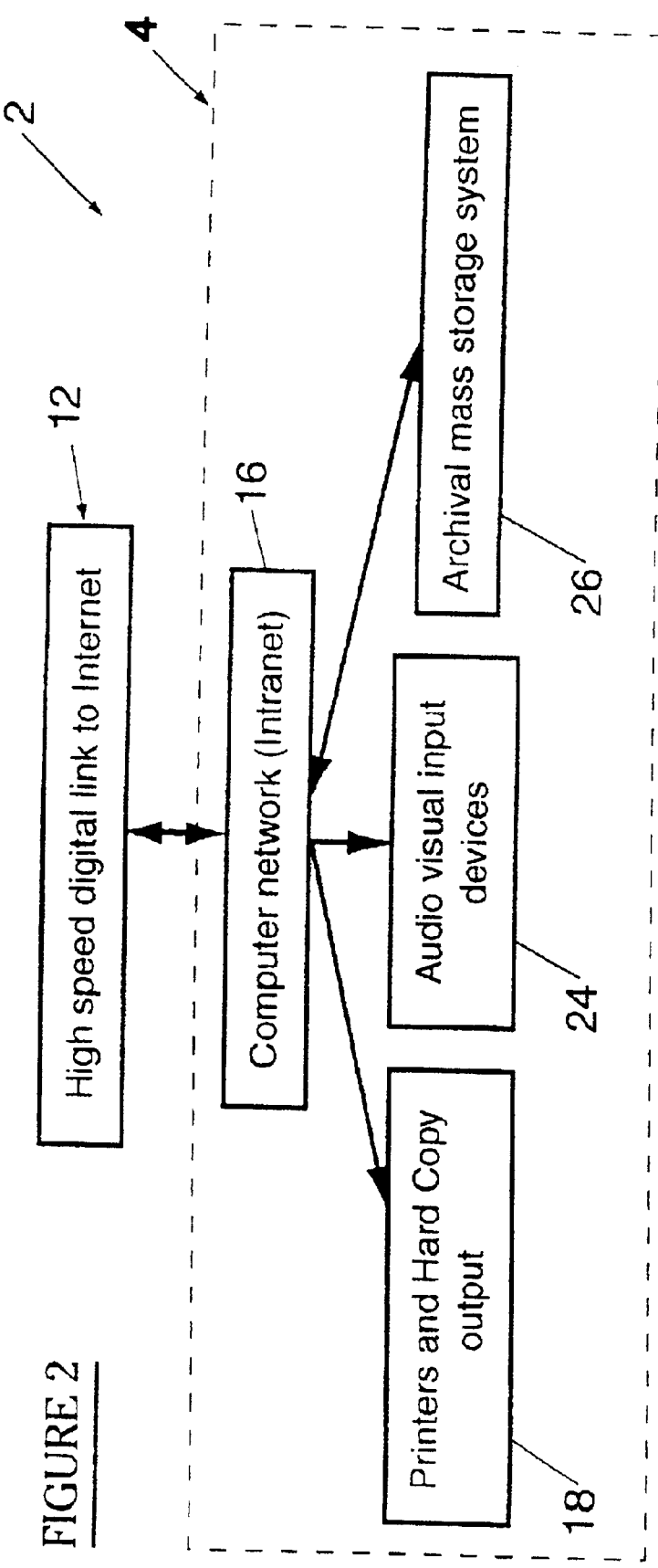
FIG. 2 is a block diagram of a central control site.

The central control site 4 is shown in more detail in FIG. 2. It comprises a central computer network 16 which is coupled for two-way conunuunication to the link 12. The network 16 preferably comprises an array of computers which are linked together to achieve the computing power necessary to process the large amount of multimedia material as well as analysing the large amount of EEG data from subjects on the Internet. Additionally, the network includes appropriate hardware and software to handle various forms of the multimedia material supplied by clients. The network 16 is coupled to output devices 18 such as printers andlor video recorders or the like. The network 16 may be coupled to a number of input devices 24 such as video and/or audio input devices for receiving material to be tested from customers. The material to be tested may comprise finished advertisements, anamatics, narrative tapes or other audiovisual or audio material which is to be tested by subjects at the test sites on behalf of the customer. The computer network 16 may be coupled to an archival mass storage system 26 for electronic storage of inputs and signals received from the remote sites. The central control site may include various output devices 28 including a printer, video recorder for producing video output for assessment and/or presentation to the customer:

The computer network 16 includes programs which utilise Fourier analysis to produce the changes in steady state response of the brain of a subject when the time varying cognitive task stimulus, such as an advertisement or audio signal or the like, is presented to the subject.

These techniques are disclosed in the aforementioned patents and therefore need not be described in detail. Alternatively, analog or hybrid circuitry may be provided at the central control site for detection of the required signals, again in accordance with the principles disclosed in the aforementioned patents.

In summary, the central control site 4 performs a number of functions including:
(i) receiving material to be tested from customers (e.g. finished ads, anamatics, narrative tapes, etc.),
(ii) producing digital multimedia test material,
(iii) downloading test sequences to specific participants,
(iv) uploading brain electrical activity information from participants,
(v) verifying participant state and quality of data,
(vi) analysing brain activity,
(vii) producing animated sequence outputs, and
(viii) producing written reports.

The central control site 4 may utilise communication software and appropriate communications hardware to receive test mnaterial from customers such as packages which are commercially available and therefore need not be described in detail. An example would be WS FrP32 or Cute FTP. Preferably, the central control site 4 is set up so that it can accept test material in all formats, hard copy, video tape and film, etc. The test material combined with information on the required demographic profiles can be used to produce multimedia test material which is transmitted via the Internet to selected test sites 6. The demographic profiles relating to the test sites 6 can be retained in the storage device 26. In addition, the multimedia test material can be stored in the storage device 26 for future use.

Brain electrical activity together with specific timing information on events in the test material is uploaded from the various test sites 6 as explained in more detail below. Preferably the data is tested at the central control site 4 to verify the identity of the participant and ascertain whether the data quality is adequate using known techniques.

The computer network 16 runs Steady State Probe Topography (SSPT) analysis software which is used to ascertain regional brain activity at scalp sites of the subjects, as will be described in more detail below. The SSPT results can be presented to the customer in an animated time series form, that is to say as a moving graph illustrating the interest of the subject to the multimedia test material. Alternatively, an illustrated written report can be presented for the customer.

Figure 3A:
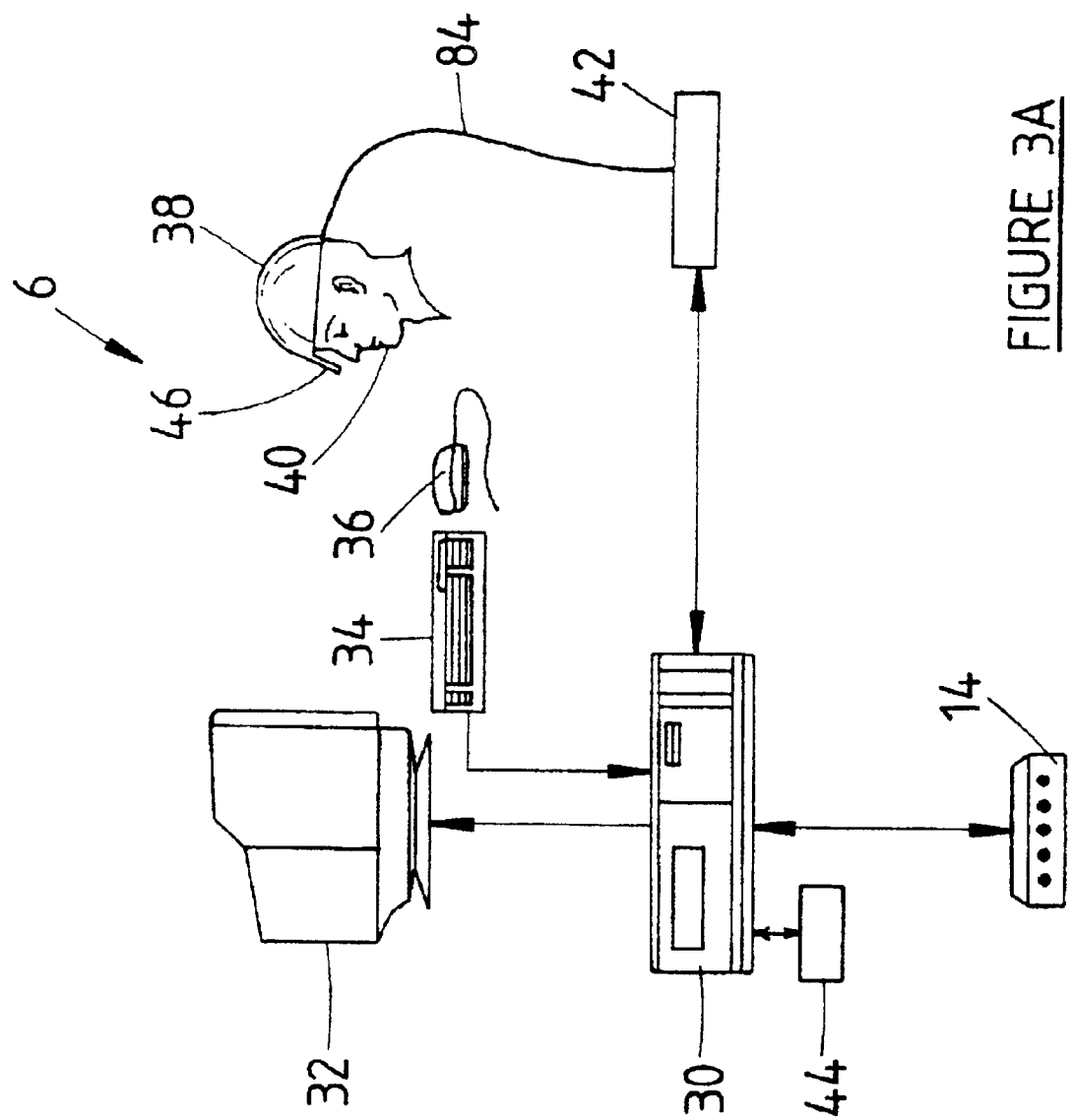
FIG. 3A is a block diagram for a remote site.

A typical test site 6 is shown in more detail in FIG. 3A. The test site 6 typically includes a computer 30 coupled to a monitor 32 or television set, keyboard 34 and mouse 36 or other pointing device. The computer 30 is coupled to the Internet 10 by means of the modem 14, as shown. The test site 6 includes a helmet 38 which is arranged to pickup electrical brain activity of the subject 40, the helmet being coupled to the computer 30 by means of a control and interface circuit 42.

Figure 3B:
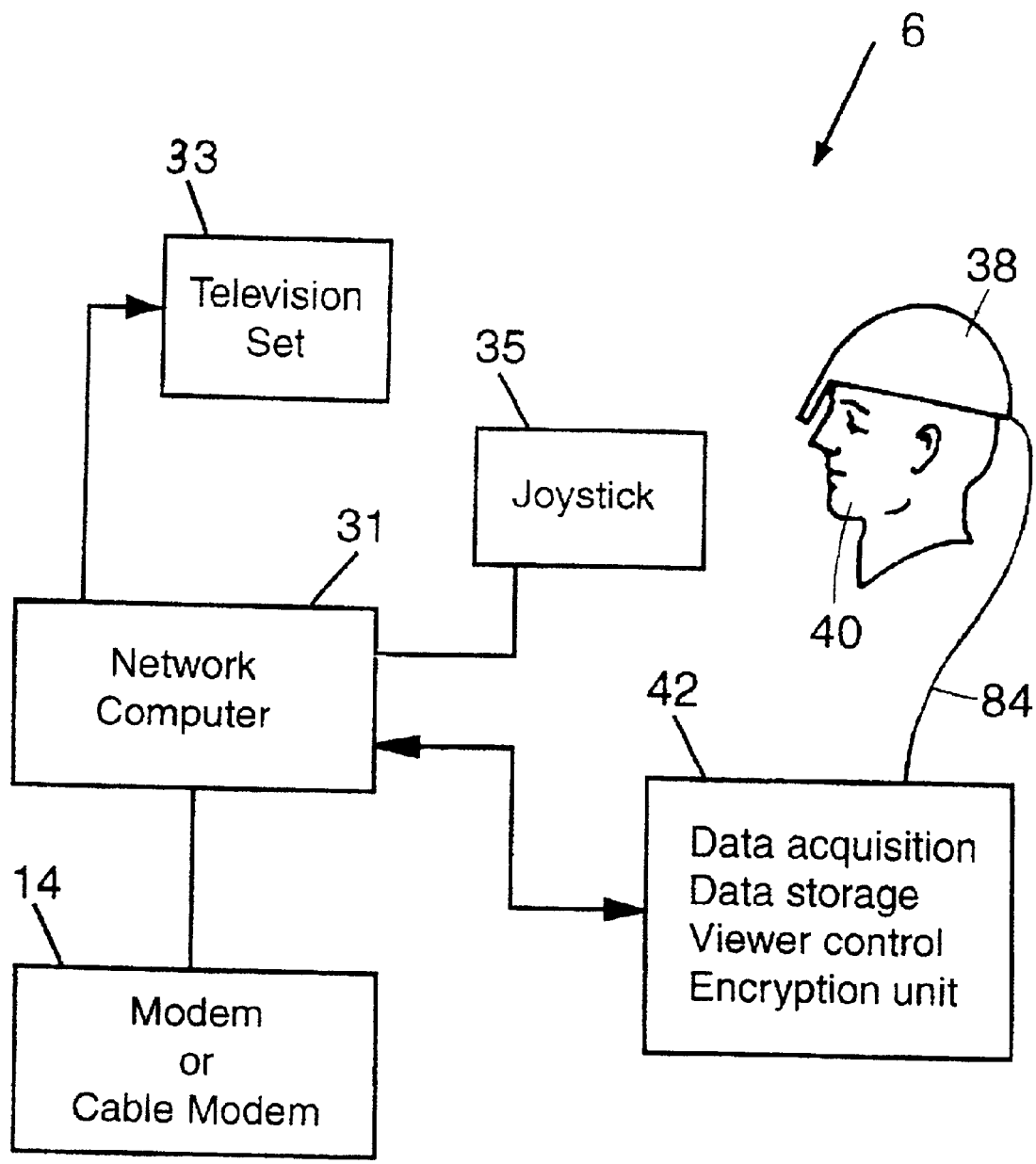
FIG. 3B is a block diagram for an alternative remote site.

FIG. 3B shows an alternative arrangement for the test site 6. This site includes a network computer 31 which is coupled to the interface circuit 42 as before. The configuration of the helmet 38 also being the same. The network computer 31 produces output to a television set 33 and receives input from a joy stick 35 which is accessible to the subject 40. The network computer 31 includes appropriate hardware or software to drive the television set 33 to display the test material to the subject.

The computer 30 preferably comprises a network computer or PC or the like which includes an additional, dedicated hard drive 44 which is used exclusively for the invention and would not normally be accessible by the subject 40. The software required for display of test material to the subject 40 and for controlling transmission of brain activity signals to the central control site 4 is preferably stored on the dedicated hard drive 44.

The helmet 38 includes a plurality of electrodes which can pickup brain activity of the subject 40. The helmet 38 includes a visor 46 through which the subject 40 can view the test material displayed on the monitor 32. The visor 46, however, provides for the display of a continuous background flicker to the peripheral vision of the user. A light sensor 48 is also mounted on the visor 46 so as to determine ambient light levels. Input to the light sensor 48 can be used to control correct lighting levels at the test site.

Signals representing electrical brain activity are detected by and recorded in the interface circuit 42. Generally speaking, the interface circuit 42 is arranged to filter and amplify the signals and then digitise and store the signals in an encrypted forrnat. The test site 6 may include programs stored on the hard drive 44 for testing the stored data to detect any EEG abnormality in the data and to provide appropriate signals to signify that further testing would be inappropriate. If the signals received by the interface circuitry 42 are, however, appropriate, the data can be transmitted to the central control site 4 via the coupling of the multimedia computer 30 to the Internet.

As indicated above, the computer 30 may comprise a standard PC or network computer which is provided with a dedicated hard drive 44 for storage of programs and data relating to the testing procedures. In the preferred arrangement, the modem 14 would normally be always turned on and, through appropriate signalling from the central control site 4, be able to activate the computer 30 so that downloading of programs and test material can be carried out. These materials would normally be stored on the dedicated hard drive 44.

Figure 5:
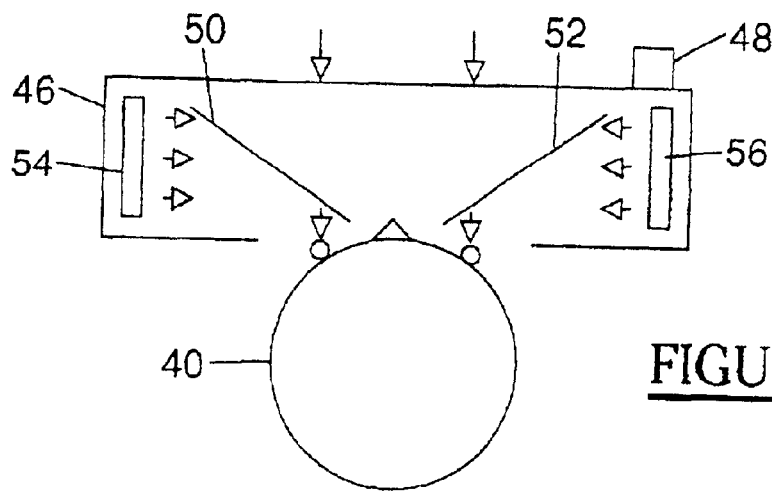
FIG. 5 is a schematic plan view showing input of signals to the eyes of a subject.
Figure 6:
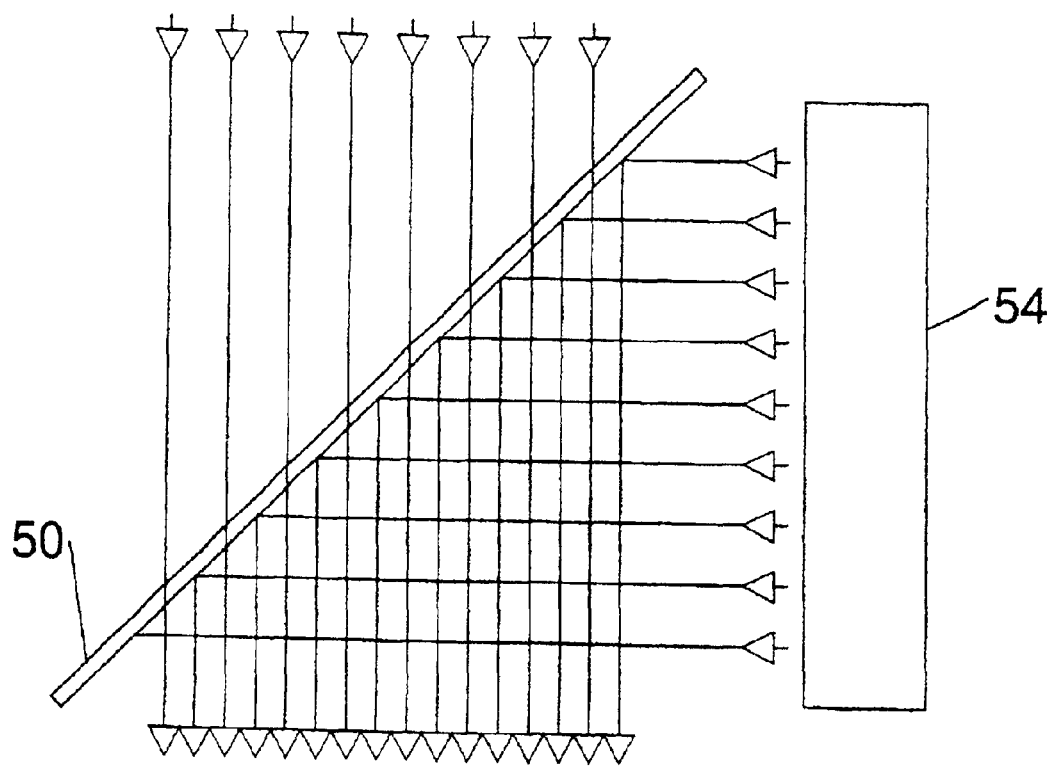
FIG. 6 shows the use of a partial mirror to combine signals to the eye of a subject.
Figure 7:
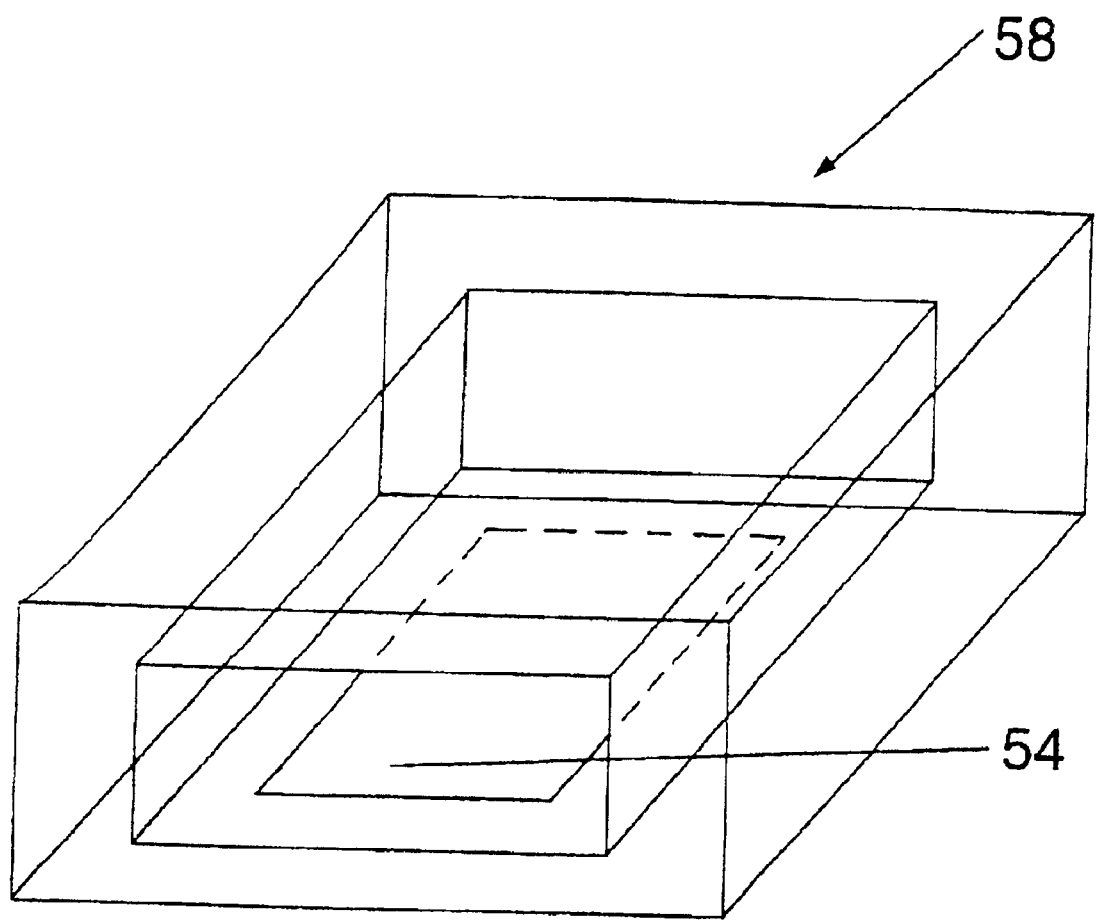
FIGS. 7, 8 and 9 are schematic views of LED shielding cages.
Figures 8, 9:
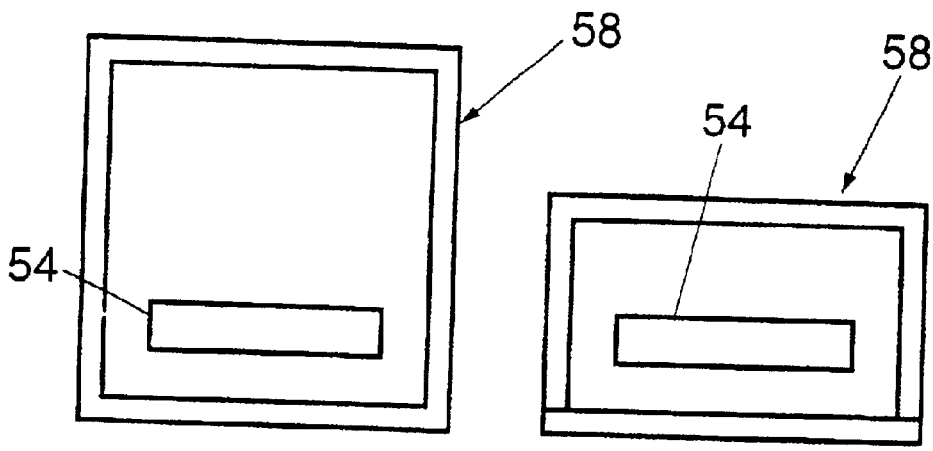
Figure 10:
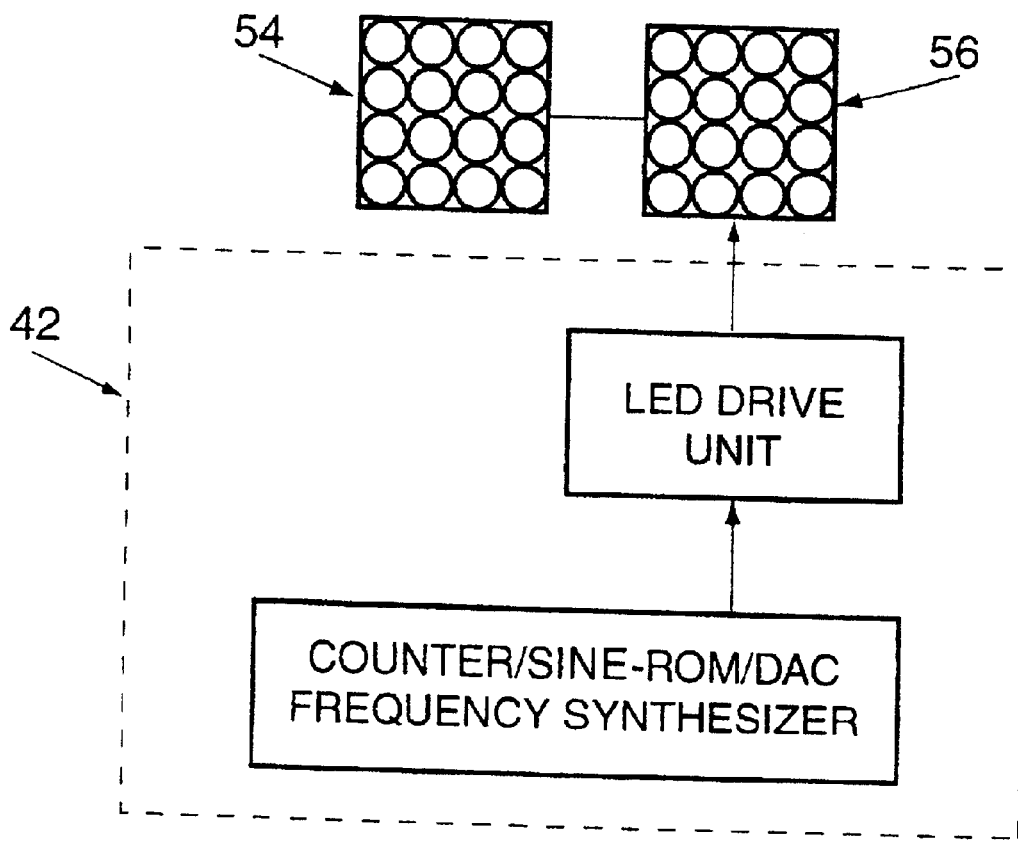
FIG. 10 is a schematic block diagram of part of the hardware at a remote site.

FIG. 5 schematically illustrates the optical components of the visor 46. The visor 46 includes two half silvered mirrors 50 and 52 which enable the subject 40 to view the monitor 32 and also to receive the controlled background flicker. The background flicker is generated by means of first and second LED arrays 54 and 56 and is reflected towards the eyes of the users through the mirrors 50 and 52. Each LED array preferably comprises nine LED devices arranged in a three by three array and located in a double Faraday cage 58 for electrical shielding. A typical Faraday cage 58 is schematically illustrated in FIGS. 7, 8 and 9.

Figure 4:
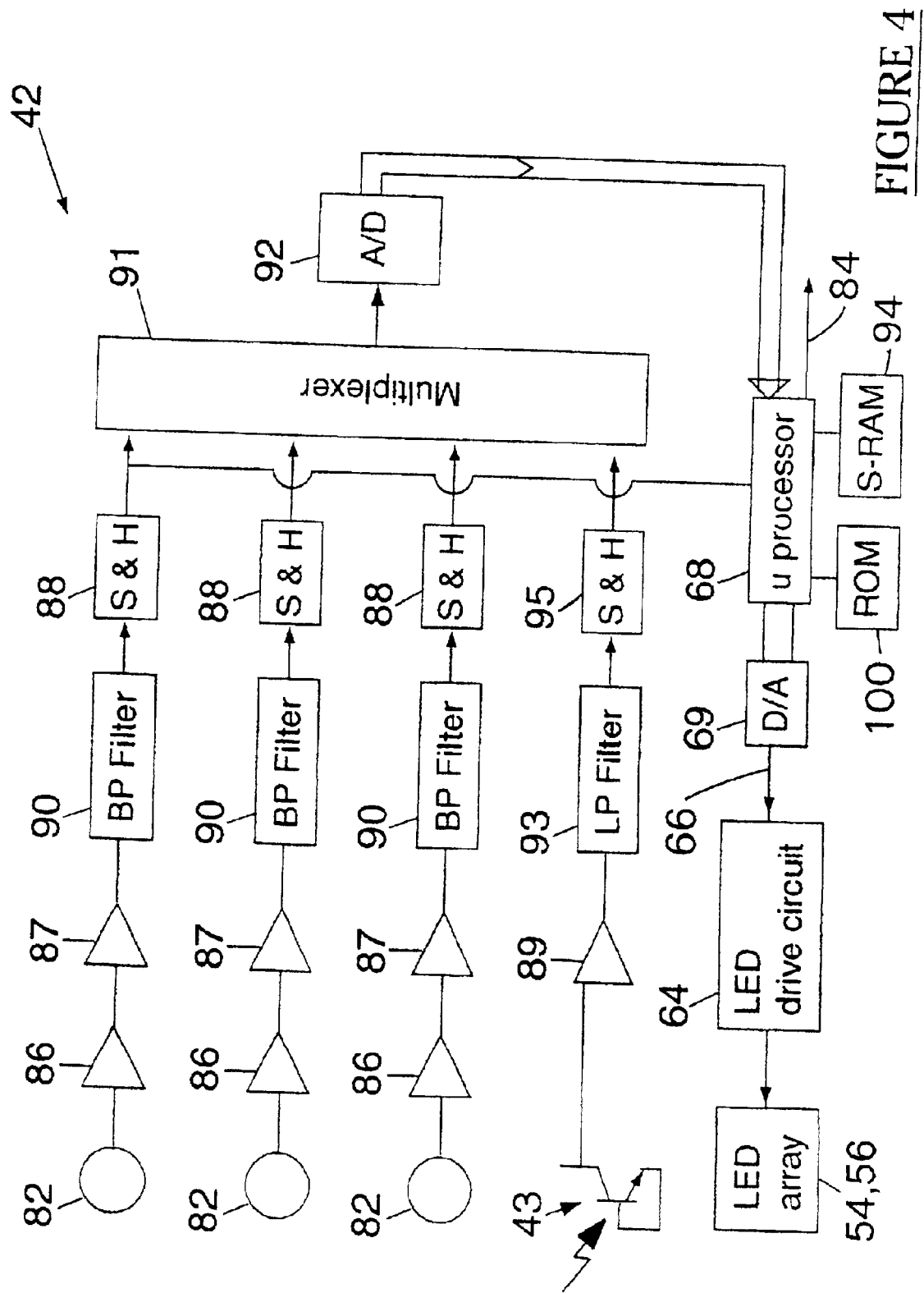
FIG. 4 is a schematic block diagram for part of the hardware at a remote site.
Figure 11:
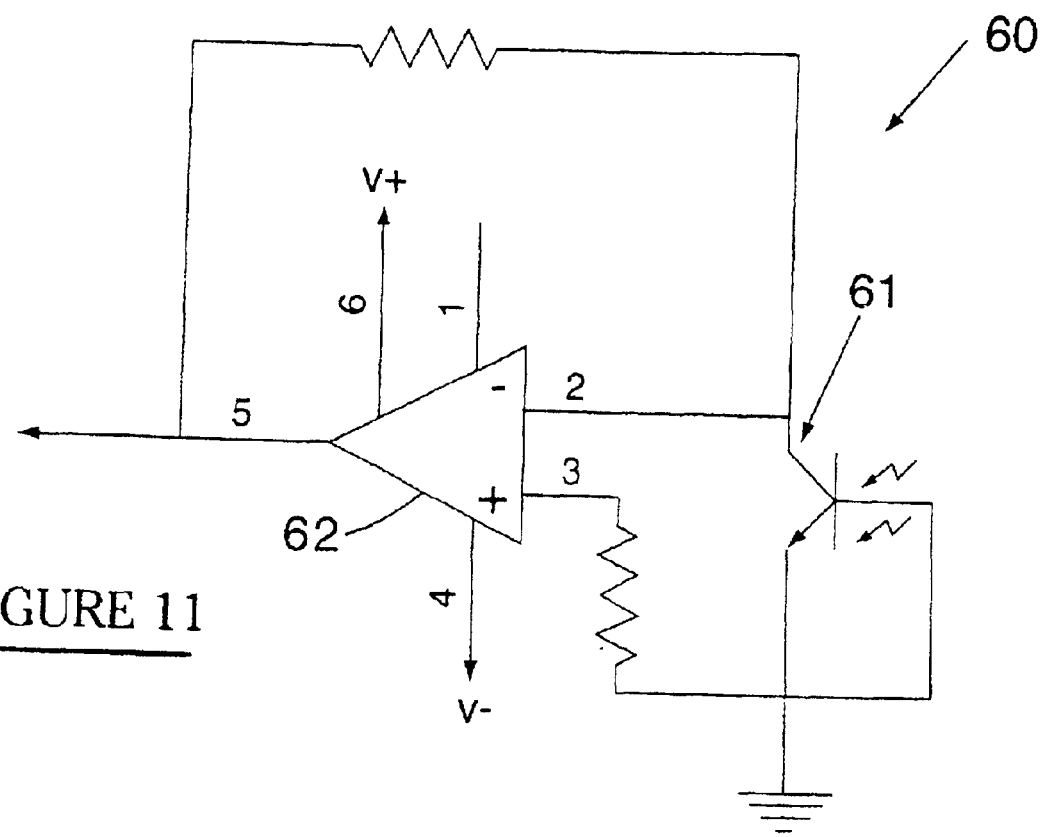
FIG. 11 shows part of an LED drive circuit.
Figure 13:
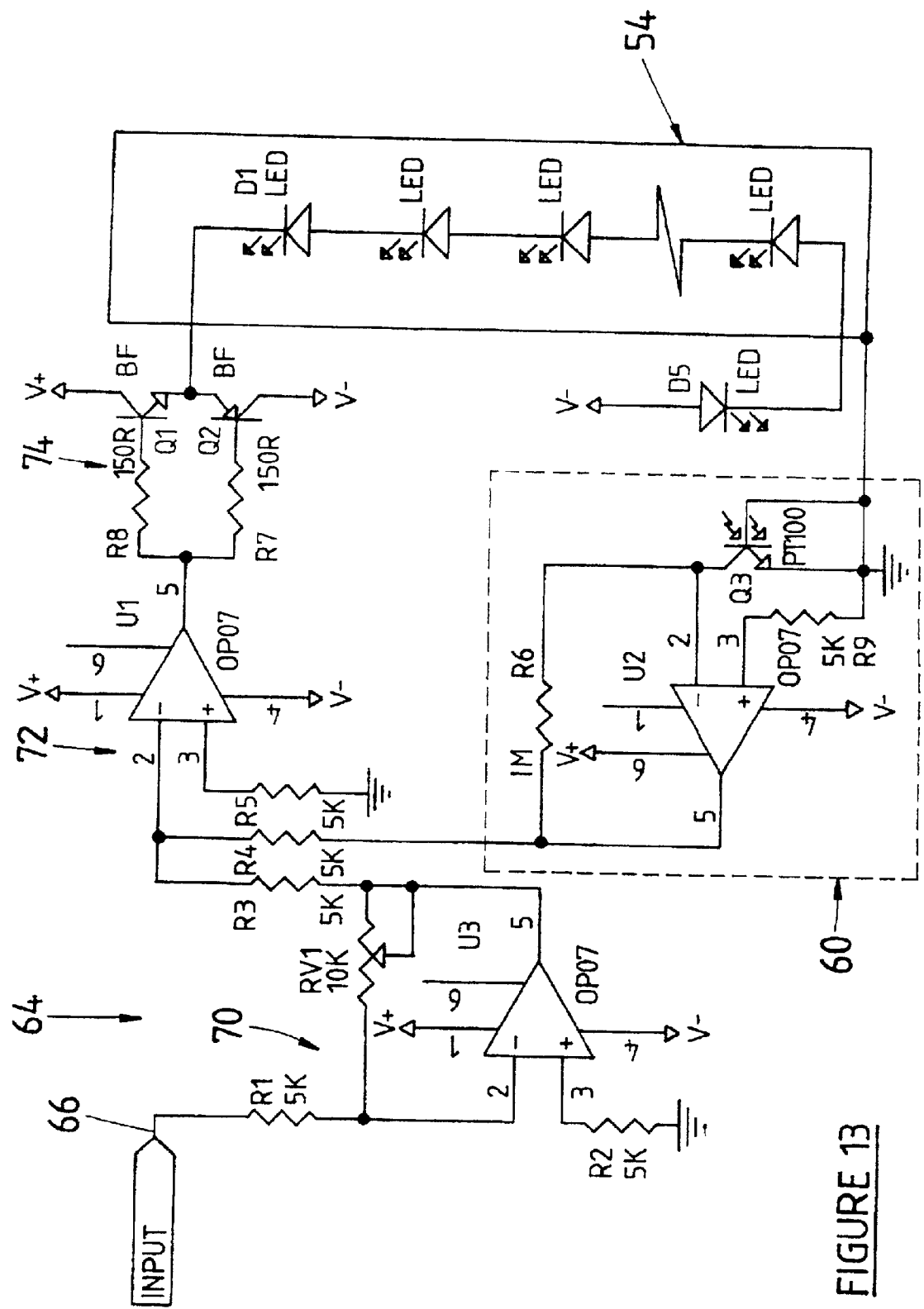
FIG. 13 shows in more detail circuitry for driving the LED array.
Figure 14:
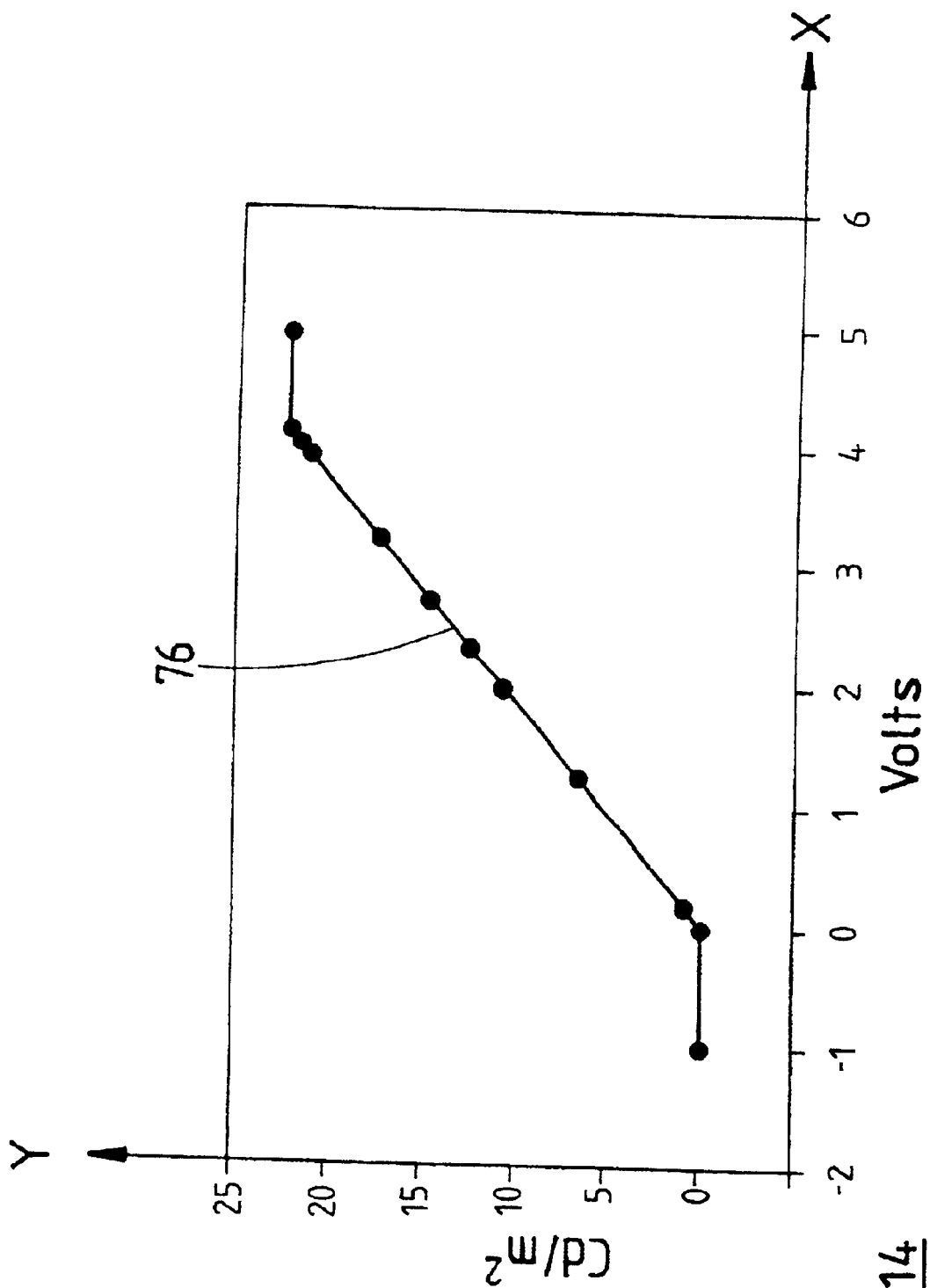
FIG. 14 shows the LED array luminance as a function of input voltage.

The luminance output of LED devices is not linear with respect to the applied voltage. Accordingly, in accordance with the invention, circuitry is provided to control the LED outputs so as to be linear. This is accomplished by using a feedback circuit 60 as shown in FIG. 11. The circuit 60 includes a phototransistor 61 coupled to the negative input of an operational amplifier 62. The phototransistor 61 is arranged to receive output from one or other of the LED arrays 54 and 56 or a further LED device connected thereto. The circuit 60 provides feedback for an LED drive circuit 64, as shown in FIG. 4. One circuit realisation for the LED drive circuit 64 is shown in FIG. 13. The drive circuit 64 includes an input 66 which receives input signals from a microprocessor controller 68 via a digital to analog converter 69. The input signals are amplified in amplifier stages 70, 72 and 74, the feedback circuit 60 provides negative feedback for the stages 72 and 74, as shown. The LED drive circuit 64 thus is able to produce a linear lurrminance output from the LED arrays 54 and 56, over a reasonable range of voltages applied to the input 66. This is graphically illustrated in FIG. 14 where the X-axis represents input voltage on the input 66 and the Y-axis represents luminance from the array 54 or 56. As indicated, the output luminance line 76 is substantially linear from about 0 volts to about 4 volts. Preferably, the LED flicker signals have a sinusoidal waveform.

The digital to analog converter 69 will produce the sinusoidal waveform when the microprocessor controller 68 sends the sine wave data held in a sine look-up table LUT stored in read only memory 100. A software counter will be used as a pointer to the sine wave LUT used to construct the sine wave. The output frequency of the waveform generator will be equal to the interrupting clock frequency divided by the number of digitised points 256 in the sine wave LUT incorporated in the program. The total harmonic distortion for a 256 point sine wave will be 0.71%. The reconstructed sine waves are then low-pass filtered by a suitable filter circuit provided in the LED drive circuit 64 to reduce the quantisation in the digitised waveforms and so reduce the total harmonic distortion.

The helmet 38 may be similar in appearance to a bicycle helmet and is used to house electrodes 82 for sensing brain electrical activity (EEG). Electrodes are preferably retracted in the helmet and a pulley arrangement may be provided to lower the electrodes to make contact with the head of the subject 40. All cabling, electronics and pulley assembly are preferably hidden inside the helmet shell with only one cable 84 connected to the rear of the helmet and extends to the circuit 42. The electrodes 82 are buffered by very high impedance unity gain amplifiers 86, as shown in FIG. 4. The electrodes are located at predetermined positions in the helmet to lineup over brain regions of interest, in accordance with known techniques.

Each of the amplifiers 86 provides a unity gain (non-inverting) with very low input bias current (1nA), very low noise (0.23uV) and additional gain is provided by very high input impedance (400 Gohm) amplifiers 87. Electrode impedance may be estimated by injecting a very small current at the electrode site through a large resistance. The electrode impedance can then be estimated as it will form one arm of a potential divider. The outputs from the amplifiers 86 are coupled to sample and hold circuits 88 via filter circuits 90 which provide band pass filtering. The band limited instrumentation amplifier will be followed by more gain and a very steep high cut-off switched filter. The switched filter will feed a two stage high cut filter (used to remove and clock feed through from the switched filter) then to the sample and hold circuits 88. The outputs of the sample and hold circuits 88 are connected to an analog multiplexer 91 and 16 bit analog to digital converter 92. The recorded EEG will normally be digitised to 16 bit accuracy. A 16 bit dynamic range means that the analog front- end gain can be fixed at a predetermiined value for all participants. As the analog multiplexer 91 is fed by individual sample and hold circuits 88 (one per EEG channel) no data time skewing will occur. All EEG data and other relevant timing information will be stored in a static random access memory (S-RAM) 94 in the interface circuitry 42. The data and timing information can then be encrypted by an encryption circuit 96 and sent to the multimedia computer 30 via a serial port 98. The computer then uploads this data to the central control site 4 via a serial link in the cable 84.

In order to maximise viewer comfort, the brightness of the visual flicker is preferably slowly increased to its final value over a period of minutes.

Figure 12:
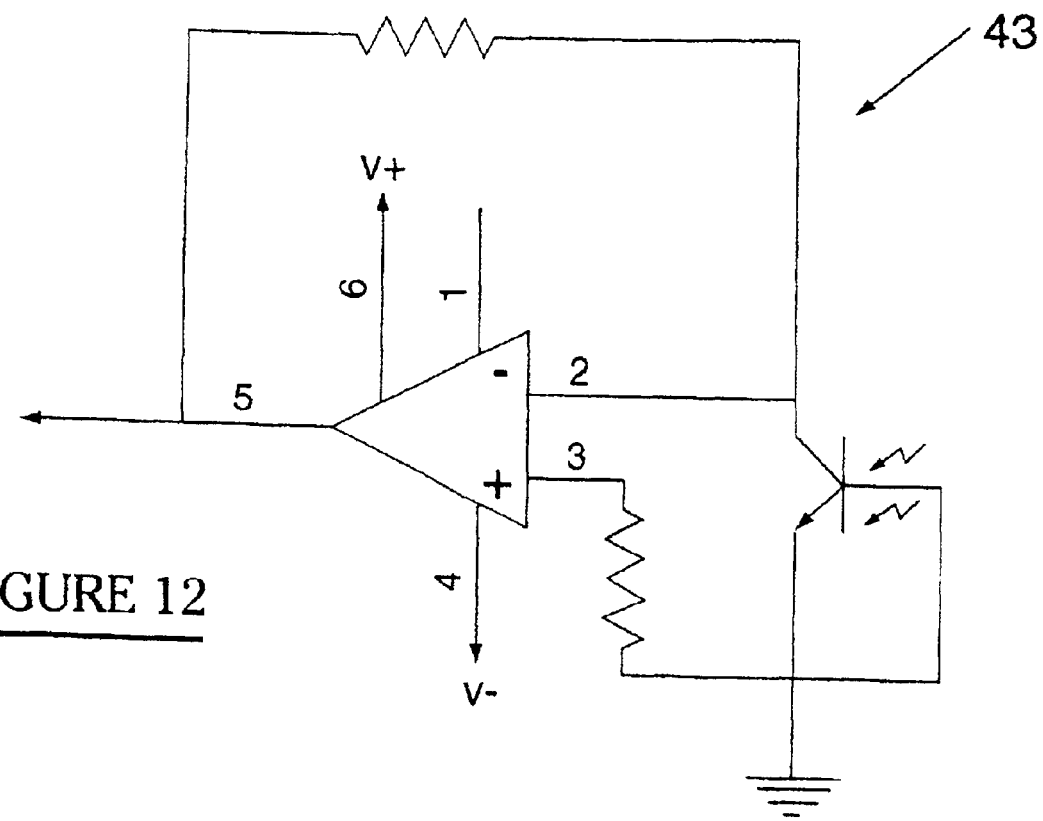
FIG. 12 shows a circuit for detecting ambient light levels.

As mentioned above, the visor includes a light detector 48 for detecting ambient light levels, the detector 48 is coupled to an ambient light level detector circuit 43, an example of which is shown in FIG. 12. The circuit 43 converts the ambient light level to a voltage signal coupled by an amplifier, low pass filter 93, and sample and hold circuit 95 to the multiplexor 91, as shown in FIG. 4. Voltage signals from the phototransistor 43 pass through the convertor 92 and are inputted to the microprocessor 68. The voltage drive from the phototransistor 43 is linearly proportional to the ambient light brightness. This voltage will be measured by software in the microprocessor to give a brightness value. If the brightness value is too high, ambient light levels are too high and a message will be generated to advise the subject to reduce the ambient light levels.

The microprocessor 68 also controls the acquisition of data by signalling the analog to digital converter 92 to measure the current EEG value at an electrode 82, as determined by the microprocessor. This data will be stored in the SRAM 94. The microprocessor with the front-end amplifiers preferably include several high accuracy 32 bit counter/timers capture circuits 102. These 32 bit counter/timers capture circuits 102 generate the timing signals for data acquisition, visual flicker frequency as well as specific events in the material tested. Such events may include the beginning and end of advertisements as well as the timing of specific events such as scene changes. The timing data held in counters 102 can be captured when signalled by the above mentioned events. The captured timing data can be stored along with the recorded EEG data in the S-RAM 94 and for later transmission and analysis. Any changes in the EEG associated with inappropriate states such as intoxication or drowsiness will be detected by software at the central control site 4 and the EEG data not used in the subsequent analysis. Software at test site may also detect any possible development of photo-epilepsy by monitoring the amplitude of the EEG at the flicker stimulus frequency. In the event of any photo-epilepsy being detected, the flicker stimulus will be discontinued and the test terminated. Subjects will be advised of the detection of drowsiness or intoxication and requested to maintain an appropriately alert state for testing.

At the end of data acquisition, the data is encrypted and transferred to the computer 30 via a serial port 98. Encrypted data will be stored on the hard drive 44 and then transferred to the central control site 4.

It will be appreciated by those skilled in the art that commercially available software packages can be utilised to perform most of the video file handling, file storage and transfer functions required in carrying out the techniques of the invention. For instance, ULead Media Studio can be used to create various multimedia test files containing the video material to be tested. Standard Internet communication software such as WS FTP32 or Cute FTP can be used to download multimedia files. These files can be compressed and encrypted using software such as WINZIP. Transfer of encrypted brain activity data can be transferred to the central control site 4 via FTP.

At the central control site 4, standard hardware and software can be used for video and audio capture and digitisation. Standard video compression techniques can also be used. It is preferred that the capture rate is thirty frames per second for video and 44 khz for audio. Normally a captured duration of up to ninety minutes would be adequate for most purposes. The video compression protocol may comprise MPEG or other similar lossless protocol.

The CPU 16 may comprise a Silicon Graphics workstation or WINTEL based system. A high security computer network "fire-wall" can be installed to reduce the risks of malicious hacking in accordance with known practice.

All multimedia material tested as well as brain electrical activity is held in the storage device 26 for ongoing access. Also, archival storage may be provided and a very high capacity tape system (at least 10,000 gigabyte) is preferred. Archiving may be done using Digital Video Disk (DVD) media.

The CPU 16 may communicate to subjects 40 at regular intervals, informing/requesting their current status and the following functions:

(i) connectivity check to subjects;
(ii) new video data to download from the server;
(iii) old video data to remove;
(iv) EEG data to upload to server; and
(v) status check of current surveys.

Preferably, all data is encrypted prior to transfer and each test site will have a unique key to decode the data.

Brain electrical activity is usually very small and may be swamped by other signal due to large movements of the participant, muscle electrical activity and mains interference. While the SSPT technology is very resistant to these interfering signals, it is desirable to monitor signal quality from all participants. A range of signal processing software may be provided to examine recorded data in both the time domain and the frequency domain to monitor noise signals.

For subjects 40 in an alert state, the brain electrical activity power spectrum and cross-spectrum can be used to verify the identity of the participant whose brain activity is being recorded. This is an important "quality control" measure.

Software in the CPU 16 calculates Steady State Visually Evoked Potential (SSVEP) amplitude and phase for each 13 Hz stimulus cycle. Calculation accomplished used Fourier techniques using equations 1.0 and 1.1.

$$a_n = \frac{1}{S\Delta\tau}\sum_{i=0}^{S-1} f(nT + i\Delta\tau)\cos\left(\frac{2\pi}{T}(nT + i\Delta\tau)\right) \quad 1.0$$

$$b_n = \frac{1}{S\Delta\tau}\sum_{i=0}^{S-1} f(nT + i\Delta\tau)\sin\left(\frac{2\pi}{T}(nT + i\Delta\tau)\right)$$

Calculation of SSVEP Fourier components where $a_n$, and $b_n$, are the cosine and sine Fourier coefficients respectively. n represents the $n^{th}$ stimulus cycle, S is the number of samples per stimulus cycle (16), $\Delta t$ is the time interval between samples, T is the period of one cycle and $f(nT+i\Delta\tau)$ is the EEG signal.

$$SSVEP_{amplitude} = \sqrt{(a_n^2 + b_n^2)} \quad\quad 1.1$$

$$SSVEP_{phase} = a\tan\left(\frac{b_n}{a_n}\right)$$

Calculation of SSVEP amplitude and phase where $a_n$ and $b_n$ are the cosine and sine Fourier coefficients respectively. Amplitude and phase components can be calculated using either single cycle Fourier coefficients or coefficients that have been calculated by integrating across multiple cycles.

Amplitude and phase time series segments are then averaged across subjects in the targeted demographic profile. Precise timing on the various events is supplied by the encrypted data file uploaded from participating subjects.

In addition to SSVEP amplitude and phase changes associated with the viewed material, it is also possible to determine the changes in the relationship between the SSVEP at different electrodes by measuring the coherence. This is similar to the correlation coefficient expressed as a function of frequency. The coherence changes with the psychological state of the subject and thus gives additional information on the response to visually presented material.

In this case, the coherence can be calculated across the subjects viewing a specific advertisement or piece of entertainment. This yields inter-electrode coherence as a function of time. Generalised the nomenclature is used below to take into account multiple subjects and multiple electrodes.

$$C_{g,d,e,n} = (a_{g,d,e,n}, b_{b,d,e,n}) \quad\quad 1.2$$

where g indexes the advertisement of film
d indexes the subjects viewing the material
e=the electrode
n=the point in time
For this calculation, the following functions are defined:

$$\gamma_{g,e1,e2,n} = H_{g,e1,e2,n} / T_{g,e1,e2,n} \quad\quad 1.3$$

$$H_{g,e1,e2,n} = \sum_{d=1}^{d=D} C_{g,e1,d,n} \cdot C^*_{g,e2,d,n} \quad\quad 1.4$$

and $$T_{g,e1,e2,n} = \sqrt{\left(\sum_{d=1}^{D} C_{g,e1,d,n} \cdot C^*_{g,e1,d,n}\right)\left(\sum_{d=1}^{D} C_{g,e2,d,n} \cdot C^*_{g,e2,d,n}\right)} \quad\quad 1.5$$

The SSVEP coherence is then given by $$\gamma^2_{g,e1,e2,n} = |H_{g,e1,e2,m}|^{2/T^2}_{g,e1,e2,n} \quad\quad 1.6$$

And the phase of the SSVEP coherence is given by $$\Phi_{g,e1,e2,n} = \text{Tan}^{-1}\left(\frac{\text{Im}(H_{g,e1,e2,n})}{\text{Re}(H_{g,e1,e2,n})}\right) \quad\quad 1.7$$

Both $\gamma^2$ and $\phi$ can be displayed as a time series and gives an indication of the psychological response associated with the cognitive task. From this indication a customer can assess the likely interest or success of an advertisement, television commercial, feature film or other audio, visual or audiovisual product.

Software to produce the animated time series ("worm") output may utilise the data from the SSPT analysis and the multimedia file holding the advertisements etc. The final output consists of an animated time series with the tested material (e.g. advertisement) presented as a multimedia animation in a corner of the screen.

Information about SSVEP amplitude and phase is preferably available for each of the recording sites. Preferably there are between 4 and 8 recording sites. Information about the brain speed and activity at the recording sites can be transformed into psychological variables such as "attention to detail" or "impact on future behaviour" and presented as animated time series.

The CPU 16 may also run software for producing written reports outlining the psychological variables during different components of the test material. The finished form of the reports may include a detailed description of the relevant psychological variable for each scene of the tested material. This may be provided for each of the target groups.

Figure 15:
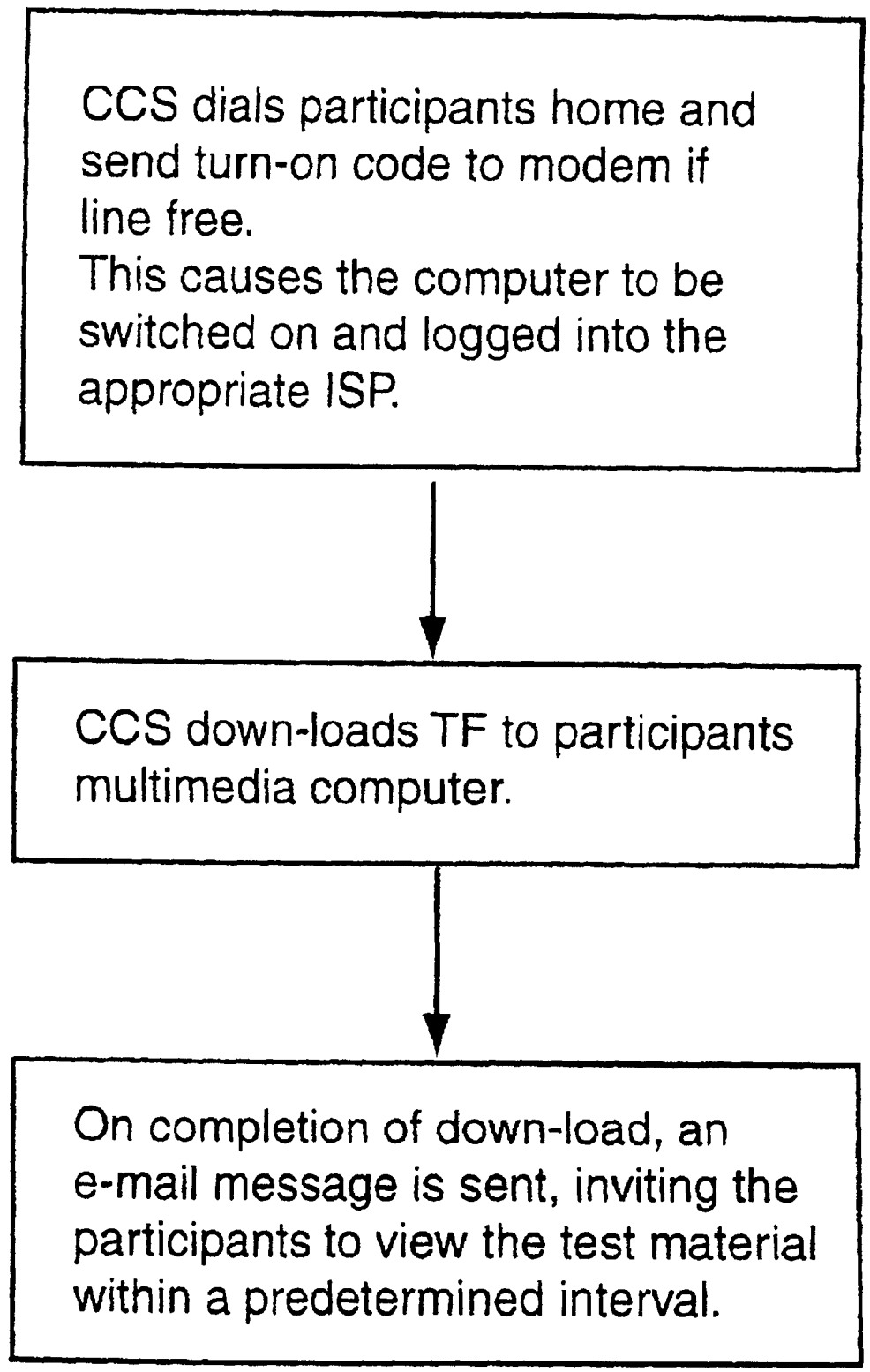
FIG. 15 shows a flow chart for part of the system.

A typical cormnercial transaction utilising the system and method of the invention typically includes the following steps:

1. A customer (advertiser, market research firm or advertising agency) wishes to test an advertising product (e.g. finished advertisement, anamatic, double head, Billboard etc.) on one or more target audience samples.
2. Advertising material is transmitted to the central control site 4 as an encrypted digital file.
3. Participating subjects at the remote sites 6 in the target group are automatically identified at the central control site 4.
4. The advertising material to be tested is-embedded in a segment of television programs relevant to the target group. Other relevant advertising material may also be embedded in the program segment to produce the Test File (TF). Multiple versions of the TF may be produced where the order of the advertisements is varied.
5. The TF is down-loaded to all relevant participants (say 100) over the Internet, using an appropriate local Internet Service Provider (ISP). Down-loading occurs automatically. This is briefly shown in the flow chart of FIG. 15.
6. Participating subjects view the material in the comfort of their home and at a time of their convenience. While this is taking place, the visual flicker is presented through the visor and brain electrical activity is recorded from the 6–8 recording sites in the helmet 38. All digitized brain activity along with timing information regarding elapsed viewing time and the visual flicker is encrypted and stored on the hard drive 44 as a Data File (DF).
7. On completion of the recording segment, the computer 30 dials in to the ISP and transfers the DF to the central control site 4.
8. Pooled time series data for each electrode and target group is generated at the central control site 4. This includes Steady State Visually Evoked Potential (SSVEP) amplitude and phase as well as inter-electrode SSVEP coherence.
9. An aniiation file is produced which illustrates the changes in SSVEP amplitude and phase for each electrode or specialised combination of electrodes. A portion of the display area includes the advertising material.
10. The animated file complete with a written report is sent to the customer. This can be sent as an encrypted file on the Internet or a dedicated communication line.

It will be appreciated by those skilled in the art that the system and method of the invention provides a powerful yet user friendly way of assessing response of target demographic groups to such things as television advertisements or the like, This can be done with a minimum of hindrance to the test subjects because they can carry out the cognitive task in their own homes and at times which suit the subject. Once the analysis has been carried out at the central control site, the results can be communicated to the customer so that the customer can then determine whether the advertisement would be successful for a particular target market. The results can indicate the subject's average response to different pans of the advertisement so that if need be the advertisement can be modified so as to increase its overall effectiveness.

Many modifications will be apparent to those skilled in the art without departing from the spirit and scope of the invention.

What is claimed is:

1. A method of mass assessment of psychological response in a cognitive task for a customer including the steps of:
   obtaining input data representing a cognitive task from a customer;
   transmitting input data signals representing the cognitive task from a central control site to a plurality of selected test sites remote from the test site over a network;
   presenting control signals simultaneously with the cognitive task to subjects at each or at least some of the selected test sites;
   detecting brain response signals from the subjects at the selected test sites to said control signals and said cognitive task;
   transmitting brain response signals to the central control site over said network;
   computing variations in brain activity of said subjects by calculating amplitude and/or phase and/or coherence of steady state visually evoked potentials (SSVEP) from said brain response signals for each selected site; and
   computing output data for the customer representing said variations in brain activity to different parts of said cognitive task.

2. A method as claimed in claim 1 including the step of storing demographic data relevant to the subject at each of said test sites; and
   selecting the selected test sites in accordance with the content of the cognitive task.

3. A method as claimed in claim 2 including the step of storing the input data signals at the selected test sites and transmitting messages to the selected test sites whereby the subjects at the test sites can activate presentation of the cognitive task.

4. A method as claimed in any one of claims 1 to 3 including the step of calculating the average amplitude and/or phase SSVEP for said selected sites.

5. A method as claimed in claim 4 wherein said detecting step includes placing electrodes adjacent to the scalp of the subject and detecting brain response signals on the electrodes and the step of computing variations in brain activity includes the step of calculating inter-electrode SSVEP coherence.

6. A method as claimed in any one of claims 1 to 5 wherein the cognitive task is an advertisement.

7. A method as claimed in claim 6 wherein the cognitive task is an audiovisual advertisement and wherein the method includes the further step of preparing a display for the customer which includes the advertisement together with output signals representative of said variations in brain activity.

8. A method as claimed in claim 1 wherein said control signals comprise visual flicker applied to the peripheral vision of the subjects.

9. A method as claimed in claim 8 including the steps of monitoring the ambient lighting levels at the selected test sites and controlling said lighting levels if they are too high.

10. A method as claimed in claim 1 including the step of increasing the brightness of the visual flicker to a predetermined value over a period of time.

11. A method as claimed in claim 7 wherein said step of preparing a display for the customer includes the step of displaying the amplitude of the SSVEP coherence as a function of time.

12. A method as claimed in claim 7 including the further step of displaying the phase of the SSVEP coherence as a function of time.

13. A method as claimed in claim 7 wherein said step of preparing a display for the customer includes the step of displaying the amplitude of the SSVEP as a function of time.

14. A method as claimed in claim 7 wherein said step of preparing a display for the customer includes the step of displaying the phase of the SSVEP as a function of time.

15. A method as claimed in claim 7 wherein said step of preparing a display for the customer includes displaying the advertisement together with output signals representative of variations in brain activity to different parts of the advertisement.

* * * * *